US012685491B2

(12) United States Patent
Roovers et al.

(10) Patent No.: US 12,685,491 B2
(45) Date of Patent: Jul. 21, 2026

(54) SYNCHRONIZING SENSORS USING HEART RATE SIGNALS

(71) Applicant: Onera Technologies B.V., Eindhoven (NL)

(72) Inventors: David Roovers, Eindhoven (NL); Tineke De Vries, Eindhoven (NL)

(73) Assignee: Onera Technologies B.V., Eindhoven (NL)

( * ) Notice: Subject to any disclaimer, the term of this patent is extended or adjusted under 35 U.S.C. 154(b) by 273 days.

(21) Appl. No.: 18/688,540

(22) PCT Filed: Aug. 17, 2022

(86) PCT No.: PCT/EP2022/072953
§ 371 (c)(1),
(2) Date: Mar. 1, 2024

(87) PCT Pub. No.: WO2023/030886
PCT Pub. Date: Mar. 9, 2023

(65) Prior Publication Data
US 2024/0366159 A1 Nov. 7, 2024

(30) Foreign Application Priority Data
Sep. 2, 2021 (EP) ..................................... 21194466

(51) Int. Cl.
*A61B 5/00* (2006.01)
*A61B 5/0205* (2006.01)
(Continued)

(52) U.S. Cl.
CPC .......... *A61B 5/7285* (2013.01); *A61B 5/0205* (2013.01); *G16H 40/67* (2018.01);
(Continued)

(58) Field of Classification Search
CPC . A61B 5/7285; A61B 5/02416; A61B 5/0006; A61B 5/0024; A61B 5/0205;
(Continued)

(56) References Cited

U.S. PATENT DOCUMENTS

| | | | |
|---|---|---|---|
| 2017/0042425 A1 | 2/2017 | Ramlall et al. | |
| 2020/0129077 A1* | 4/2020 | Rogers ................. | A61B 5/0004 |
| 2021/0275110 A1* | 9/2021 | Tomlinson ........... | A61B 5/6833 |

FOREIGN PATENT DOCUMENTS

| | | | | |
|---|---|---|---|---|
| EP | 3865059 A1 * | 8/2021 | ............. | A61B 5/352 |

OTHER PUBLICATIONS

International Search Report and Written Opinion for International Application No. PCT/EP2022/072953, mailed Nov. 23, 2022, (15 pages).

(Continued)

*Primary Examiner* — Carl H Layno
*Assistant Examiner* — Anh-Khoa N Dinh
(74) *Attorney, Agent, or Firm* — Kagan Binder, PLLC

(57) ABSTRACT

A method of synchronizing output signals from a plurality of sensors each measuring a heart rate derivable physiological signal of a subject along with a physiological signal of interest includes acquiring first and second output signals using respective first and second sensors, where each sensor includes an independent clock for associating its output signal with a respective time domain. The method further includes determining first and second heart rate sequence signals from the first and second output signals, identifying timings of at least one heart rate event in the respective first and second heart rate sequence signals, and determining a first time domain transformation for the time domain of the second output signal to the time domain of the first output (Continued)

signal using a model fitted to the timings of the heart rate event in the respective first and second heart rate sequence signals.

15 Claims, 7 Drawing Sheets

(51) Int. Cl.

| | |
|---|---|
| *A61B 5/0245* | (2006.01) |
| *A61B 5/332* | (2021.01) |
| *A61B 5/349* | (2021.01) |
| *A61B 5/353* | (2021.01) |
| *G16H 40/67* | (2018.01) |
| *A61B 5/024* | (2006.01) |

(52) U.S. Cl.
    CPC ....... *A61B 5/02416* (2013.01); *A61B 5/02438* (2013.01); *A61B 5/332* (2021.01); *A61B 5/4806* (2013.01)

(58) Field of Classification Search
    CPC .... A61B 2560/0233; A61B 2560/0412; A61B 5/0008; A61B 5/0022; A61B 5/0026; A61B 5/01; A61B 5/02055; A61B 5/021; A61B 5/0215; A61B 5/022; A61B 5/024; A61B 5/031; A61B 5/0816; A61B 5/1112
    See application file for complete search history.

(56)                    References Cited

OTHER PUBLICATIONS

Lemay et al., "Wrist-located optical device for atrial fibrillation screening: A clinical study on twenty patients," 2016 Computing in Cardiology Conference, 43; pp. 681-684, Sep. 11, 2016, (4 pages).

* cited by examiner

SYNCHRONIZING SENSORS USING HEART RATE SIGNALS

CROSS-REFERENCE TO RELATED APPLICATIONS

This application claims priority to International Application No. PCT/EP2022/072953, filed Aug. 17, 2022 and titled "SYNCHRONIZING SENSORS USING HEART RATE SIGNALS," which in turn claims priority from a European Patent Application having Ser. No. 21/194,466.5, filed Sep. 2, 2021, both of which are incorporated herein by reference in their entireties.

TECHNICAL FIELD

The present disclosure relates to a method of synchronizing output signals from a plurality of body worn sensors, and especially sensors each measuring a heartbeat derivable physiological signal of a subject.

BACKGROUND

Wearable sensors may be used to measure physiological signals in a subject simultaneously at different locations on the body. For improved user comfort such sensors are preferably wireless. Since the sensors have independent clocks which drift relative to each other, this introduces the problem that the captured signals are not synchronized in time. In order to use the output signals of the sensors for joint manual determination or in an automated process, the signals need to be synchronized.

There are known technologies used for synchronization of output signal from such wearable sensors. There are for instance methods relying on wirelessly sending and/or receiving time information during measurement, and others that rely on a posteriori signal analysis.

However, methods relying on time information in the wireless transmissions during measurement puts high requirements on the wearable sensors, such as high power needs, device complexity etc., which increases battery size requirements and costs for the sensors. Further, such requirements on the sensors increases the risks related to loss of connectivity and security vulnerability. Further, known methods relying on a posteriori signal analysis require certain activities from the subject in order enable a posteriori synchronization, such as certain movement or gestures. Such requirement on the subject makes the method unreliable since it would be unpredictable how a subject would perform the required activities.

Consequently, there is a need for a method for synchronizing the output signals of a plurality of wearable sensors on a subject that is more reliable, robust and accurate.

SUMMARY

It is an object of the present invention to provide an improved solution that alleviates the mentioned drawbacks with present solutions. Furthermore, it is an object to provide a method and a system for synchronizing output signals from a plurality of sensors configured to measure heartbeat derivable physiological signals of a subject in a way that is reliable, robust and accurate.

The invention is defined by the appended independent claims, with embodiments being set forth in the appended dependent claims, in the following description and in the drawings.

According to a first aspect of the invention, this is provided with a method of synchronizing output signals from a plurality of sensors each measuring a heartbeat derivable physiological signal of a subject. The method comprises the steps of providing a first output signal acquired by means of a first sensor configured to measure a heartbeat derivable physiological signal of a subject; providing a second output signal acquired by means of a second sensor configured to measure a heartbeat derivable physiological signal of the subject, wherein each of the first and second sensor comprises an independent clock for associating the first and second output signals with a respective time domain. The method further comprises the steps of: determining a first heart rate sequence signal from the first output signal; determining a second heart rate sequence signal from the second output signal;

identifying timings of at least one heart rate event in the respective first and second heart rate sequence signals; and determining a first time domain transformation for the time domain of the second output signal to the time domain of the first output signal by means of a model fitted to the timings of the at least one heart rate event in the respective first and second heart rate sequence signals. Further, the method comprises the steps of providing a first additional physiological signal captured by means of the first sensor, which first additional physiological signal is different from the first output signal, providing a second additional physiological signal captured by means of the second sensor, which second additional physiological signal is different from the second output signal, and applying model parameters of said model to said first additional physiological signal and said second additional physiological signal to synchronize the first and second additional physiological signals.

The first sensor may be considered as a reference sensor, and the second sensor may be considered as a target sensor. The purpose of the present method may then be to synchronize the output signal from the target sensor to the clock domain of the reference sensor. In further embodiments, the method may comprise synchronizing output signals from a plurality of target sensors with the reference sensor.

The disclosed method for synchronization may not operate on detected heart beats directly. Instead, the determination is performed on heart rate sequence signals derived from the sequences of heartbeat time stamps in the output signals. A heart rate event may be a segment of a heart rate sequence.

The first and second sensors may be body worn sensors, which may be arranged on e.g. the chest, leg or head of the subject. One of the sensors may be a flow sensor. Each of the sensors captures one or more physiological signals. The signals measured by the sensors needs to be synchronized in time in order to be jointly presented to a user, or to be processed by an automated method. The sensors may, prior to performing measurements and being subject to a synchronization, be jointly connected and configured to a control unit. The sensors may be wireless and once disconnected they have no means of communication between each other. Each sensor has an independent clock which may drift relative to the other sensor clocks. The present method of synchronization may thereby be needed for a posteriori synchronization of the recorded physiological signals.

For the purpose of synchronization, each of the sensors may be designed to have the additional capability of measuring a cardiac signal or heartbeat derivable physiological signal along with the physiological signals of interest. The acquired cardiac signals can be used to synchronize the sensors since they originate from one and the same source, i.e. the electrical activity of the sinus node, which controls the pumping activity of the heart.

A purpose of the present method may be to identify synchronization parameters by making use of naturally occurring heart rate variability in subjects. The method may match heart rate sequence patterns observed in the output signals and fits a model for clock drift to make the matching segments coincide in time.

The model parameters identified by the method may then be applied to the other physiological signals captured by each of the sensors.

During for instance a sleep study, the signals from sensors need to be mutually synchronized throughout the study. Functionally, this may mean that any event which is observed in two sensors and which, from a physical point of view, is known to manifest itself simultaneously in the two sensors, may also be observed to be simultaneous in the output signals. In some embodiments, the observations being simultaneous may be considered up to a maximum allowed time misalignment. In one embodiment, the maximum allowed misalignment may be set to 1 s.

In clinical practice, a time misalignment of 1$s$ may still be perceived as significant, especially when viewing clearly demarcated events. As an example, when the subject wearing the sensors is snoring, each occurrence may be clearly visible in output signals of two sensors, such as a nasal cannula signal recorded by a flow sensor and a sound signal recorded by a chest sensor. Observing a time misalignment between these signals which should be simultaneous may be confusing to a clinician and even lead to an incorrect diagnosis. Therefore a maximum time misalignment of no more than approximately 250 ms may be considered as preferable.

According to one embodiment, the step of determining a first time domain transformation may comprise the steps of identifying a first time difference between the timing of a first heart rate event in the first heart rate sequence signal and the timing of a corresponding first heart rate event in the second heart rate sequence signal, and forming the model based on the first time difference. The first time difference may thereby provide information on how the time domains of the first and second sensors differ. The applied model may be based thereon to define the first time domain transformation for the second output signal.

According to one embodiment, the step of determining a first time domain transformation may further comprise identifying a second time difference between the timing of a second heart rate event in the first heart rate sequence signal and the timing of a corresponding second heart rate event in the second heart rate sequence signal, and the step of forming the model may comprise a step of forming a linear model based on the first and second time differences. The step of identifying timings of heart rate events in the heart rate sequence signals may thereby comprise identifying timings of at least two heart rate events in the heart rate sequence signals. By identifying a second time difference, the relationship between the first and second time differences may be determined. The change in time difference between the first and second time differences may indicate a drift of the time domain of the second sensor compared to the time domain of the first sensor. Based on this a linear model may be applied for the first time domain transformation to the second output signal and/or other signals measured by the second sensor. The method may further comprise determination of additional time differences, e.g. a third time difference, a fourth time difference, and so forth, based on further heart rate events. The additional determined time differences may be used to additionally form the linear model. Using additional time differences may provide additional robustness and accuracy of the model.

According to one embodiment, the first heart rate sequence signal may be based on a portion of the first output signal and the second heart rate sequence signal is based on a portion of the second output signal. A predetermined time range of the output signals may be used for the identification of heart rate events. In some embodiments, a determined heart rate sequence signal may be redefined based on one or more heart rate events in either of the heart rate sequence signals being determined as unsatisfactory or missing.

According to one embodiment, the method may further comprise a step of resampling the second output signal based on the first time domain transformation. Hence, the entire second output signal may be resampled using the first time domain transformation in order to synchronize the second output signal with the first output signal. In one embodiment, further signals that may have been measured by the second sensor may alternatively or additionally be resampled using the first time domain transformation.

According to one embodiment, the linear model may be described as $A+Bt_2$, wherein A may represent an initial time offset between the first and second heart rate sequence signals, B may represent a clock drift of the clock of the second sensor based on the first and second time differences, and $t_2$ may be the time instant of the time domain of the second output signal. The initial time offset may be provided by the first time difference, i.e. the time difference between the first identified heart rate event in the respective heart rate sequence signals. The clock drift may be determined from the difference between the first and second time differences identified for the first and second heart rate events in the respective heart rate sequence signals. This may provide a linear model to apply to the second output signal and/or another signal from the second sensor.

According to one embodiment, at least one of the first and second sensors providing the first and second output signals may be a body-worn sensor. Preferably all sensors may be body-worn sensors. The body-worn sensors may be configured for wireless communication to a control unit. According to one embodiment, said body-worn sensor/sensors may be configured to be worn on the chest, the head, and/or a leg of a subject.

According to one embodiment, at least one of the sensors providing an output signal may be an ECG-measuring sensor. According to one embodiment, at least one of the sensors providing an output signal is a PPG-measuring sensor. The type of sensor, for measuring ECG or PPG, may be selected based on where on a subject's body the sensor is configured to be attached to measure a signal. This may further depend on requirements on accuracy on the measurement and flexibility in location of the sensor.

According to one embodiment, the method may further comprise the steps of providing a third and fourth output signal each acquired by means of a respective third and fourth sensor measuring a heart rate derivable physiological signal of a subject, and determining a second and a third time domain transformation for the time domains of the third and fourth output signals to the time domain of the first output signal by means of respective models fitted to the timings of heartbeats in the respective first and third heart rate sequence signals and first and fourth heart rate sequence signals, respectively. When up to four sensors are used in the measurement, the output signals of these four sensors may need to be synchronized. The present method may then be applied of the respective output signals. The first output signal may be used as a reference signal, and time domain transformations may be applied to the second, third and fourth output signals, and/or on other signals from the second, third and fourth sensor. Further features discussed above for the embodiments using a first and a second sensor may be equally applied to the embodiments comprising additionally a third sensor and optionally also a fourth sensor.

According to one embodiment, two of the first, second, third, and fourth sensors may be ECG-measuring sensors. According to one embodiment, two of the first, second, third, and fourth sensors may be PPG-measuring sensors.

According to one embodiment, the method may be applied to a measurement of a subject during a sleep cycle. The method of synchronizing the signals may be applied offline after the measurement on the subject has been performed. In a sleep cycle measurement, heart rate or detection of heartbeats may typically be a part of the measurement. At least a portion of the sensors used may be configured for mainly measuring other signals than heartbeat/heart rate, but may be configured to measure heartbeat/heart rate additionally for the purpose of synchronization.

According to one embodiment, the step of identifying at least one heart rate event in the first and second heart rate sequence signals may comprise a step of identifying the respective heart rate event in the first and second heart rate sequence signals as corresponding if the identified timings of the heart rate events has a maximum allowed misalignment. The maximum allowed misalignment may be set to ensure that two identified heart rate events in the respective heart rate sequence signals are correctly determined as corresponding. If the timings of the two heart rate events differ too much in the time domains of the clocks, i.e. outside the maximum allowed misalignment, it cannot be ensured that the heart rate events in fact originate from the same heartbeat. Such timing comparison may thereby be uncertain and may thereby be disqualified. If the timing of a heart rate event is determined to be outside the allowed misalignment, new heart rate event(s) may be identified to be used for the determination of the first time domain transformation. The maximum allowed misalignment may be before synchronization. The clocks of the first and second sensors may have been configured to the same time at an initial point of time, such as prior to shipping to the user. Since the clocks of the two sensors may drift over time, by time of using the sensors, the time of the clocks may differ. The difference may depend on the accuracy of the clocks and the time elapsed between configuration and application. When synchronizing the sensors, it saves e.g. necessary computation if the matching heart rate events are not spaced e.g. several hours in the respective time domains of the clocks of the sensors. The maximum allowed misalignment may therefore, in different embodiments be set to up to 5 minutes, up to 30 seconds, or up to 5 seconds. This may further make the method more robust.

In one embodiment, the plurality of sensor may comprise four sensors; a chest sensor, a head sensor, a leg sensor and a flow sensor. The chest and flow sensors may measure ECG, and the head and leg sensors may measure (reflective) PPG.

The used modality may depend on the location of the sensor. While ECG may provide the most accurate result, it may be measured only on certain locations on the body. PPG, on the other hand, may be measured on a wide range of locations on the body.

According to a second aspect of the invention, a system for synchronizing sensor output signals is provided, the system comprising: at least a first and a second sensor each configured to measure a heartbeat derivable physiological signal of a subject and to provide a first and second output signal, respectively, wherein each sensor comprises an independent clock for associating the first and second output signals with a respective time domain; and a processing unit. The processor unit is configured to: receive the first and second output signals; determine a first heart rate sequence signal from the first output signal; determine a second heart rate sequence signal from the second output signal; identify timings of at least one heart rate event in the respective first and second heart rate sequence signals; and determine a first time domain transformation for the time domain of the second output signal to the time domain of the first output signal by means of a model fitted to the timings of the at least one heart rate event in the respective first and second heart rate sequence signals. Further, the first sensor is configured to capture a first additional physiological signal which is different from the first output signal, and the second sensor is configured to capture a second additional physiological signal which is different from the first output signal, and the processing unit is configured to apply model parameters of said model to said first and second additional physiological signals to synchronize said first and second additional physiological signals. The system may further be configured to perform the method according to any of the embodiments described above.

BRIEF DESCRIPTION OF THE DRAWINGS

The invention will in the following be described in more detail with reference to the enclosed drawings, wherein.

DESCRIPTION OF EMBODIMENTS

Figure 1:
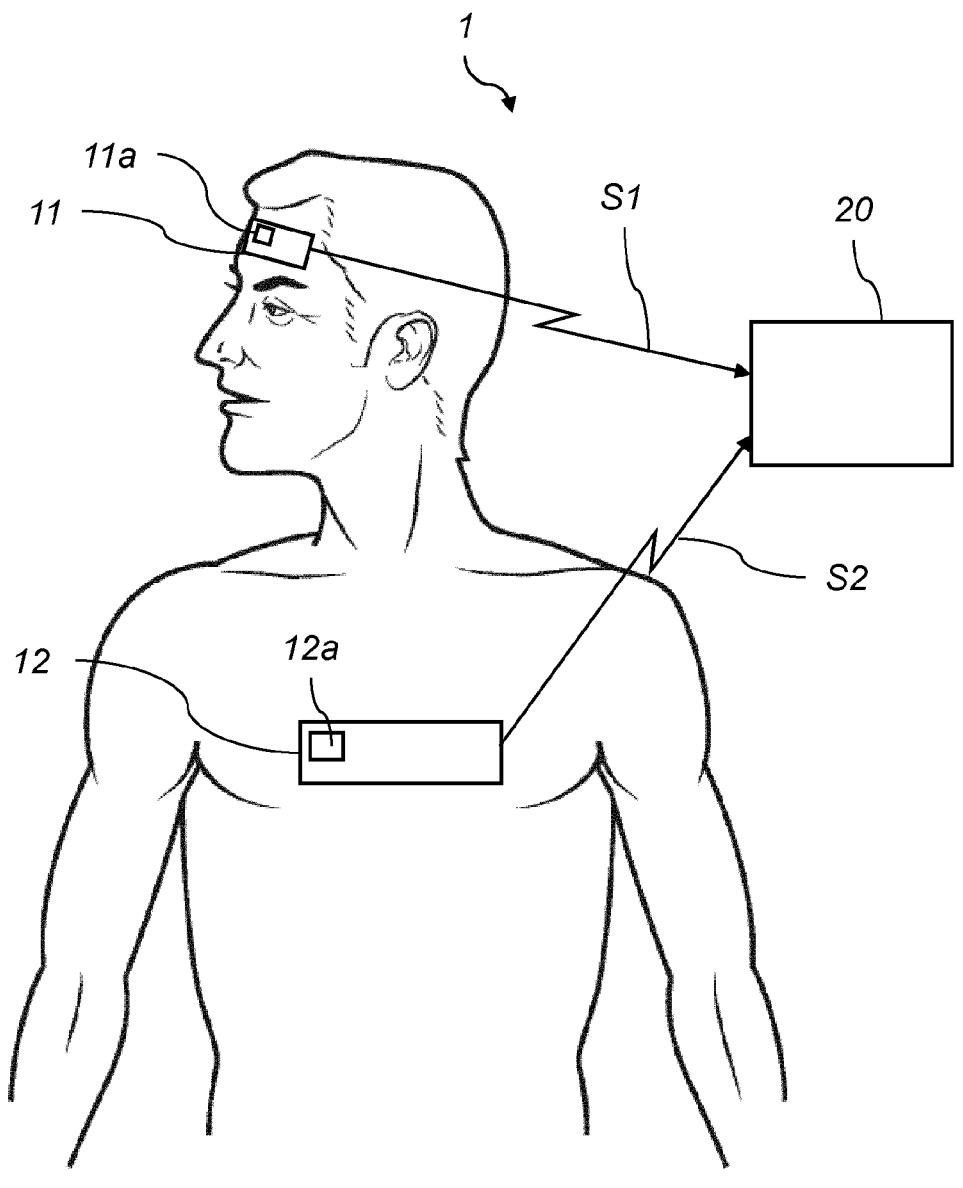
FIG. 1 shows a system according to one embodiment of the invention.

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

FIG. 1 illustrates a system 1 comprising a first sensor 11 and a second sensor 12 arranged on a subject for measurement of physiological signals, and a control unit 20. Each sensor 11, 12 is configured for measurement of at least one physiological signal, including a cardiac signal. The sensors 11, 12 are wireless sensors, transmitting respective output signals S1, S2 to the control unit 20. The sensors 11, 12 each comprises an individual clock. The output signals S1, S2 are synchronized by the control unit 20. The output signals S1, S2 are the measured cardiac signals. Each sensor 11, 12 may also transmit to the control unit 20 other physiological signals measured.

Amongst other signals, sensors 11, 12 both capture the cardiac signal, S1($n$) and S2($m$) respectively, which may be either an ECG or a PPG signal. The signals are sampled at time instants t1($n$) and t2($m$), according to the respective sample clock. Both t1 and t2 are measured relative to the start of the recording for the corresponding sensor.

The cardiac signals S1, S2 are driven by cardiac activity, provided as a sequence of either ECG complexes or PPG pulses. Each of these heart beats may be time stamped by a beat detector function. If the corresponding heart beats in output signals S1 and S2 are matched, synchronization information from their respective time of occurrence according the respective sensor's sample clock may be derived.

From the output signals S1, S2, a respective first and second heart rate sequence signal r1($n$) and r2($m$) are determined. Each is sampled on a uniform time grid in the corresponding sensor's 11, 12 time domain.

Figure 2:
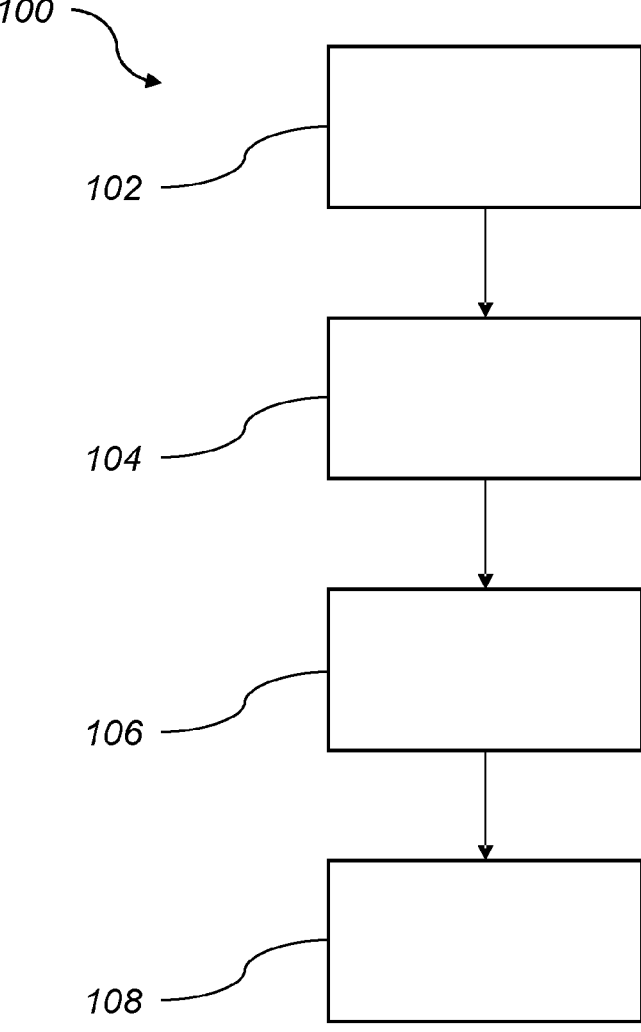
FIG. 2 shows a flow chart of a method according to one embodiment of the invention.

FIG. 2 illustrates a method 100 according to an embodiment of the invention. The method 100 comprises a step of providing 102 the first output signal S1 acquired by means of the first sensor 11 configured to measure a heartbeat derivable physiological signal of a subject, and the second output signal S2 acquired by means of the second sensor 12 configured to measure a heartbeat derivable physiological signal of the subject. Each of the sensors 11, 12 comprises an independent clock 11a, 12a for associating the first and second output signals S1, S2 with a respective time domain. Further, the method 100 comprises a step of determining 104 the first heart rate sequence signal r1 from the first output signal S1 and the second heart rate sequence signal r2 from the second output signal S2. Next, the method 100 comprises a step of identifying 106 timings of at least one heartbeat in the respective first and second heart rate sequence signals r1, r2. Finally, the method 100 comprises a step of determining 108 a first time domain transformation for the time domain of the second output signal S2 to the time domain of the first output signal S1 by means of a model fitted to the timings of the at least one heartbeat in the respective first and second heart rate sequence signals r1, r2.

Figure 3A:
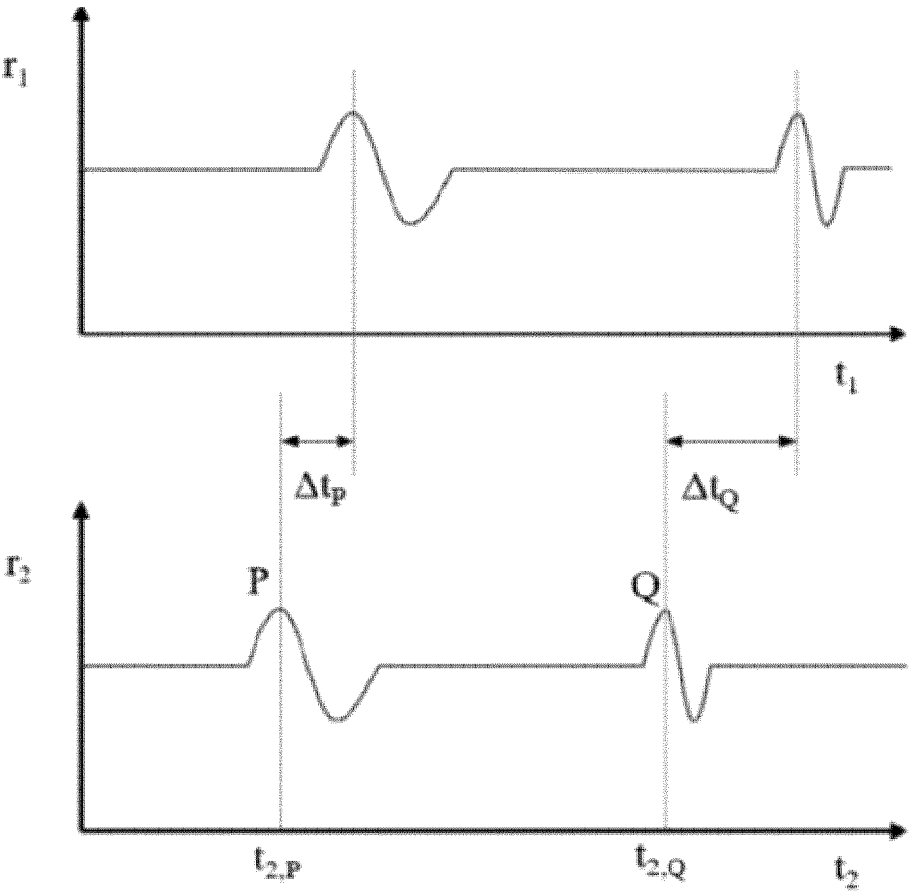
FIG. 3a shows graphs of heart rate sequence signals according to one embodiment of the invention.

FIG. 3a shows heart rate sequence signals r1, r2 measured by the first and second sensors 11, 12. Points P and Q mark events or patterns in the heart rate sequence signals r1, r2. Hence, in this embodiment two heart rate events are identified in the respective heart rate sequence signals r1, r2. Event P occurs in r1 with a delay ΔtP relative to r2. Event Q occurs in r1 with a delay ΔtQ relative to r2. The synchronization provides a time domain transformation which maps t2 to t1 and, by resampling, transform signal r2 to the clock domain of r1 such that events P and Q occur simultaneously in both signals. This same time domain transformation can then also be applied to the entire second output signal S2 and/or other signals measured by the second sensor 12.

Figure 3B:
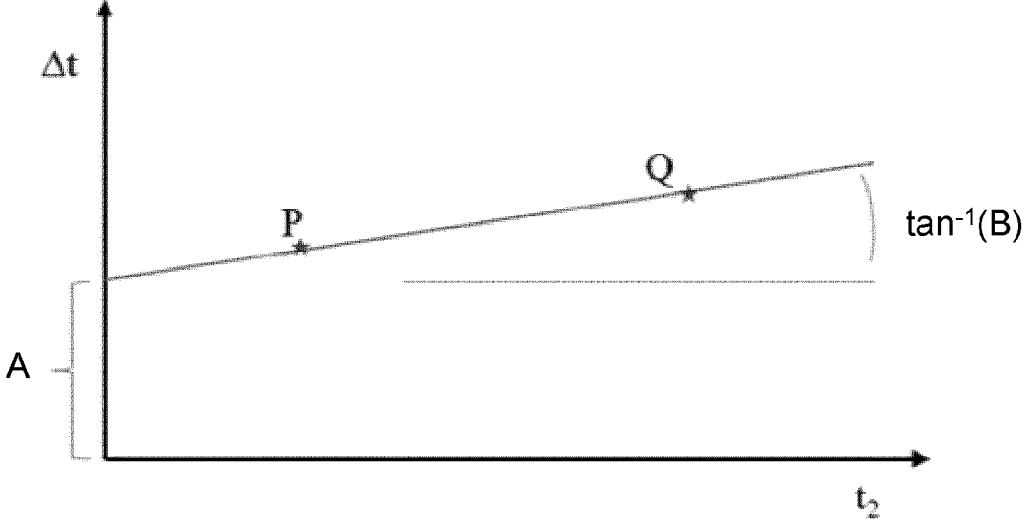
FIG. 3b shows a graph of a time delay as a function of $t_2$ according to one embodiment of the invention.

FIG. 3b shows the time delay Δt as a function of t2, with events P and Q marked as stars. It also shows a straight line fitted to P and Q, which provides a linear model for the time domain transformation. The linear model may be described as $$\Delta t = A + Bt2,$$

with parameter A representing the initial time offset and B representing the clock drift. This model assumes a linear increase of Δt over time, i.e. a constant clock drift B.

Note that the model Δt=A+Bt2 can also be written as t1=A+(1+B)t2. The latter equation provides how to transform t2 into t1 with the purpose of resampling the signals of the second sensor. The plotting of Δt on the vertical axis reveals any deviation from perfectly synchronized clocks as a non-horizontal line not passing through the origin. Directly plotting t1 as a function of t2 would hardly reveal this information, since the time differences are very small compared to the elapsed time itself.

Each sensor 11, 12 has a real time clock and an acquisition clock. The real time clock is used to retrieve the local date and time of events, such as the start of a recording. It is set upon configuration of the sensors 11, 12 for the intended study, such as a sleep study, and remains powered regardless of the sensor state. The acquisition clock drives the signal sampling by the sensor front ends and the creation of records, and is only active when the sensor is in powered state.

Therefore, assuming that in reality the sensors 11, 12 started measuring at exactly the same moment, the initial time offset A defined above must be attributed to the accumulated drift of the RTCs between the time of sensor configuration and the start of the measurement. Additionally, a truncation error may be introduced because the start time of a recording is represented in integer seconds. The drift parameter B is entirely determined by the acquisition clocks.

The two sensors 11, 12 are generally not started exactly simultaneously. Each sensor 11, 12 uses its RTC to report the start time of its recording, denoted as Ts,1 and Ts,2, respectively. If the RTCs are fully synchronized, this would result in a known initial time offset ΔTs≙Ts,2–Ts,1.

If considering the unknown part caused by clock drift, the model may be refined as:

$$\Delta t = \Delta Ts + A + Bt2.$$

As stated above, a linear model having a single parameter B for the drift in the acquisition clocks may be applied. This model assumes that the acquisition clocks 11a, 12a are stable during a measurement (i.e. the dependence of the oscillator frequency on variations in temperature and voltage is sufficiently low), and that there are no data losses (frame drops) in the data acquisition.

Parameters A and B may not take arbitrary values. Their ranges are determined by the specifications of the clocks 11a, 12a and the use case. Since robustness of the synchronization to errors is of prime importance to a clinical use case and is considered as a risk management measure for the system, increasing this robustness by limiting the range of estimated parameters based on prior knowledge may be relevant.

The maximum absolute initial time offset $A_{max}$ may be determined by the maximum absolute RTC drift $d_{RTC,max}$ and the maximum lead time $T_L$, max between configuring the sensors in a station and starting the recording:

$$A_{max} = 2T_{L,max} \cdot d_{RTC,max}.$$

The factor of 2 accounts for the fact that the RTCs may drift in opposite directions. The specified maximum drift of the sensors 11, 12 may be 1 s in 24 hours (11.5 ppm). Assuming a maximum lead time of 5 days, it provides $A_{max}$=10 s.

The range of parameter B may be determined by the maximum drift of the acquisition clocks: $b_{max}$=2$d_{acq,max}$. The sensors 11, 12 may have a specified Overall Frequency Stability of ±25 ppm or ±50 ppm. The sensors may in one embodiment be implemented with a value $b_{max}$=50 ppm.

Figure 4:
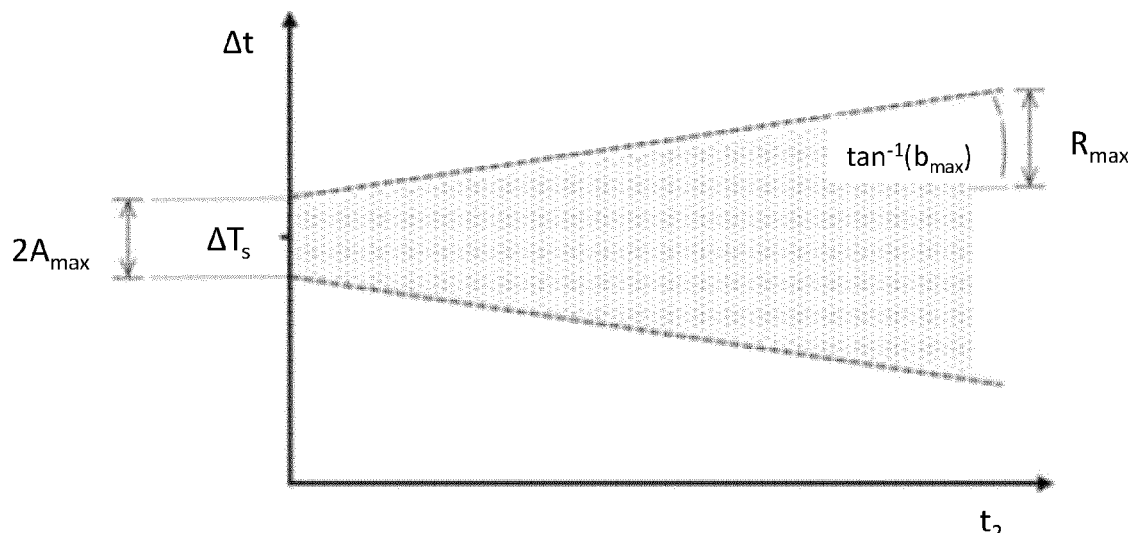
FIG. 4 shows a graph of ranges of parameter B according to one embodiment of the invention.

The parameter ranges described above are visualized in FIG. 4. Here, $R_{max}$ represents the maximum time shift that may be accumulated during the recording: $R_{max}$=$D_{ovl}b_{max}$, where $D_{ovl}$ is the duration of the overlapping part of the two recordings. It may be assumed for simplicity that the recordings are fully overlapping, then $D_{ovl}$ equals the minimum of the recording durations: $D_{ovl}$=min (D1,D2).

As described above, the synchronization is based on matching heart rate sequence patterns in the two sensor output signals S1, S2. Further details are presented below.

The matching may operate on the interpolated heart rate sequence signals r1($n$) and r2($n$), each sampled at a uniform sample rate $f_{s,int}$. The second heart rate sequence signal r2 may be divided into overlapping segments with a segment length L and a shift S between segments (expressed in samples). In one implementation embodiment, the corresponding segment duration is 90 s while the shift equals 60 s.

Each segment, which may be a heart rate event, may be compared to a range of segments in the first heart rate sequence signal r1 having the same length L but shifted in time. The range of time shifts may be determined by the start time offset $\Delta$Ts and the maximum expected time shift $R_{max}$. The time shift resulting in the best match between r1 and r2 may be selected.

In one implementation embodiment, the similarity between segments from the heart rate sequence signals r1 and r2 is expressed as the mean of the absolute differences (MAD) between the samples. This may provide the cost function:

$$\vartheta(k, d) = \frac{1}{L} \sum_{l=1}^{L} \text{abs}\{r_1(kS + l + d) - r_2(kS + l)\}.$$

Here, k is the segment index, d is the sample shift between r1 and r2, and L and S are the segment length and segment shift, respectively. For a given value of the segment index k, the cost function may be evaluated for all delay values in the range of interest D={$d_{min}$, . . . $d_{max}$}. Referring back to FIG. 4, it may be provided:

$$d_{min} = (\Delta Ts - A_{max} - R_{max})f_{s,int}$$

$$d_{max} = (\Delta Ts + A_{max} + R_{max})f_{s,int}$$

Then the minimum of the cost function may be determined as:

$$\delta(k) = \underset{d \in D}{\text{argmin}}\{\vartheta(k, d)\},$$

$$\vartheta_{min}(k) = \vartheta(k, \delta(k)).$$

Having found the minimum, its location and value may be further refined into $\tilde{\delta}$ (k) and $\tilde{\vartheta}$min(k) by local parabolic interpolation of $\vartheta$(k,d).

For reasons of processor efficiency, the vector of mean absolute differences and its minimum may first be calculated on subsampled heart rate segments. A sample rate $f_{s,low}$=4 Hz may be obtained by skipping samples. Having found the minimum, its location may be refined by locally repeating the procedure at the original sample rate $f_{s,int}$.

The matching procedure described above may always provide a match, since it only looks for the minimum of the cost function. It may be considered to impose an acceptance criterion to make it further useful. In one implementation embodiment, a data point {k,$\tilde{\delta}$(k)} is accepted in first instance if the corresponding mean absolute difference $\tilde{\vartheta}$min (k) is below 1.5 bpm.

Further, note that the matching procedure may assume that r1 and r2 represent valid heart rate sequences. However, each of the sequences may contain gaps where no heart rate could be determined. These are indicated by zero-valued heart rates. If the current segment of either r1 or r2 contains one or more gaps, the segment may be excluded from matching by assigning to it a high value of $\tilde{\vartheta}$min(k).

Figure 5:
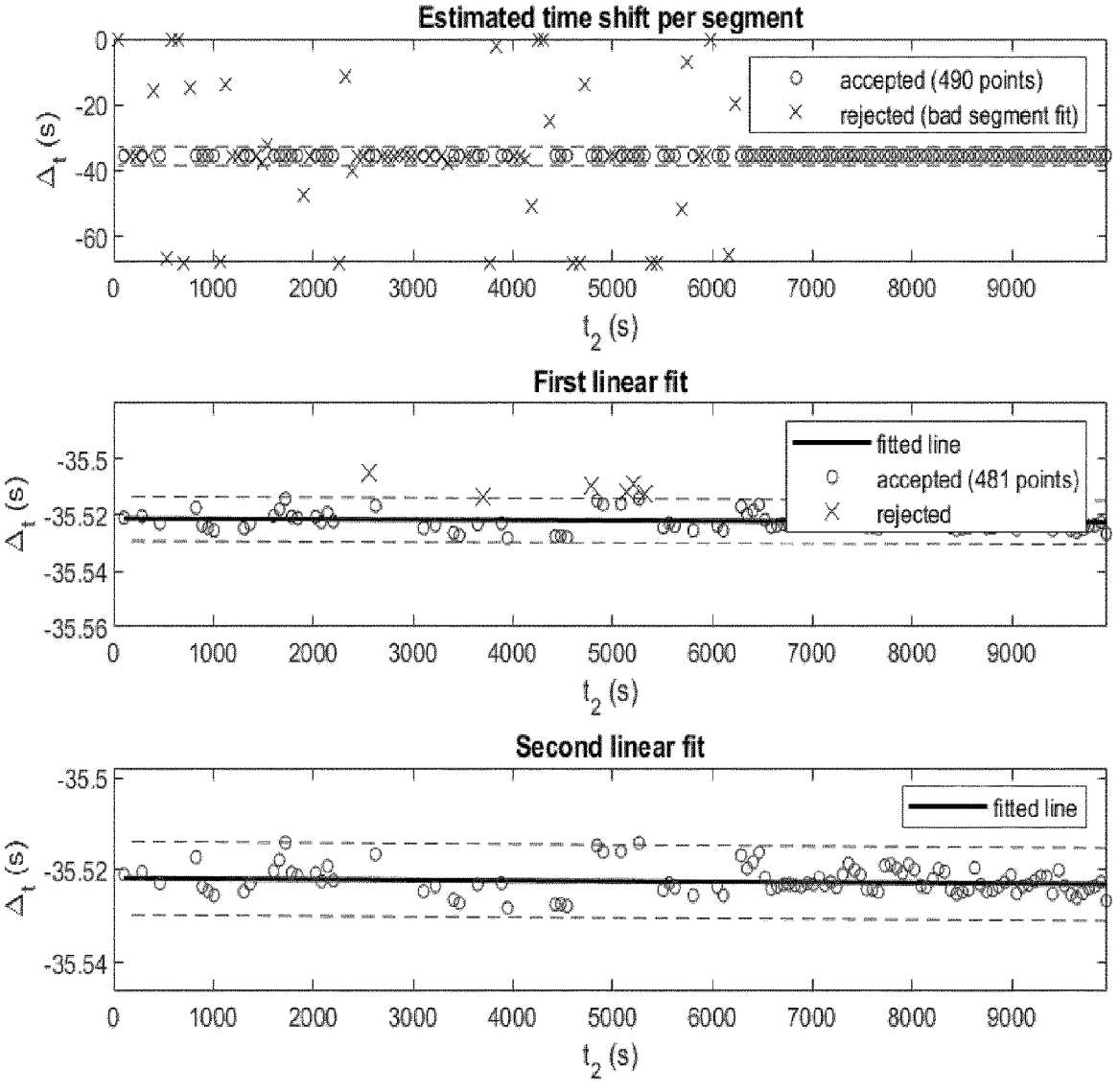
FIG. 5 shows scatter plots of data points according to one embodiment of the invention.

After the application as above to all segment shifts k it may be created a scatter plot of $\Delta$t versus t2 by substituting $t_2$(k)=kS$f_s$ and $\Delta$t(k)=$\tilde{\delta}$(k)$f_s$. FIG. 5 (top pane) shows an example of such a scatter plot. In this plot, the crosses indicate data points which were rejected because of a bad match between segments.

Further, a fitting of a line to the data points may be applied. While doing so, care may need to be taken to effectively remove outliers. The occurrence of outliers in the scatter plot may be attributed to (at least) two causes: Heart rate segments that may be far apart in time may still match by coincidence. This may typically result in a very small number of outliers, but potentially with very high errors; Errors in the heart rate sequences (e.g. missed beats, inserted beats or interpolations) may shift the minimum of the MAD away from its true location. This may typically lead to smaller, but more frequent errors.

To cope with such outliers, the linear regression may be performed in two steps. Before fitting the first line, any far outliers are excluded based on their deviation from the median value $\Delta$t$_{median}$. Above it was described that the maximum time shift $R_{max}$ which may be accumulated during a recording may be determined by the maximum mutual clock drift and the common recording duration. Using this, any data point having a time difference $\Delta$t deviating by more than $R_{max}$ seconds from the median value $\Delta$t$_{median}$ is rejected.

After this outlier rejection a first linear model is fitted to the data (see FIG. 5, middle pane). Then, from the data and the model the standard deviation may be calculated. Its value is used to do a second rejection of outliers based on a relative measure: data points deviating from the model by more than 2.5 standard deviations may be discarded.

Following this second rejection of outliers, a second linear model is fitted to the remaining data points (see FIG. 5, bottom pane). Here, the dashed lines indicate 2.5 standard deviations.

The above described method 100 may further comprise a step of assessing whether the synchronization was successful. If not, an error may be reported and signals from the sensor for which the synchronization failed may not be included in the system output. The assessment may comprise three criteria.

From the available data points and the estimated model, it may be estimated the sample variance $\sigma^2$ as $$\hat{\sigma}^2 = \frac{\sum_i (\Delta t_i - \Delta t_{fit,i})^2}{n_{eff} - 2},$$

where $\Delta t_{fit,i} = \hat{a} + \hat{b} t_{2,i}$. In this equation, $n_{eff}$ is the effective number of samples, which is smaller than the actual number of samples n in case of overlapping segments:

$$n_{eff} = \frac{S}{L} n.$$

The value of $\hat{\sigma}^2$ is a measure for the deviations between the data points and the model. A too high value indicates that something is wrong: either the data points might be too much affected by noise, or the model assumptions may not hold (e.g. because of clock instability or data loss).

When assessing the sample variance, natural variability in the data may be taken into account especially for heart rate derived from PPG, because of nightly variations in pulse arrival time.

Figure 6:
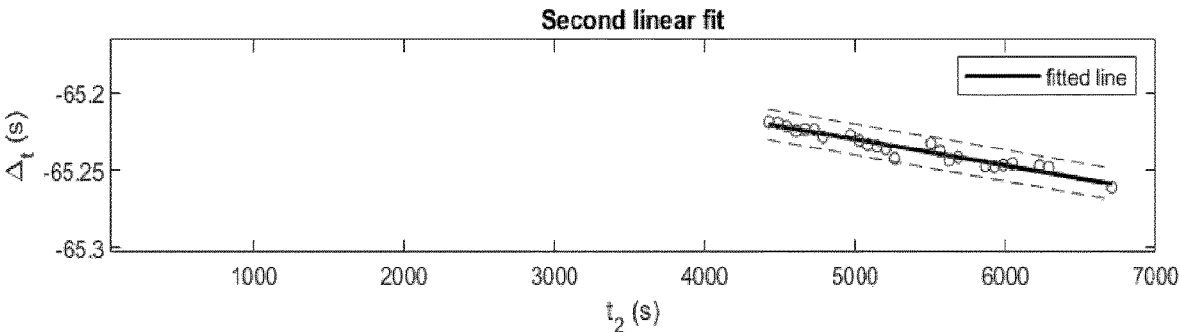
FIG. 6 shows a plot for model accuracy estimation according to one embodiment of the invention.

The criterion above may be necessary, but not sufficient to assess the quality of the synchronization. It may also be needed to estimate the accuracy of the model when applied to the data, as explained by FIG. 6. The graph shows how the model may be fitted to data points that cover only a part of the recording. It may be understood that the error in the model at time instances $t_2$ far away from the available data points may be larger than for time instances which are closer, and that it depends on the accuracy of the drift estimate $\hat{b}$.

Assuming that we have an estimate of the sample variance $\hat{\sigma}^2$, the variance of the estimator $\hat{b}$ may be estimated as $$\hat{\sigma}_b^2 = \frac{\hat{\sigma}^2}{\sum_i \left(t_{2,i} - \overline{t_2}\right)^2}$$

Where $\overline{t_2}$ denotes the average value of $t_2$. Note that the denominator in this equation represents the variance of $t_2$, and this since the larger the spread in $t_2$, the better the drift b may be estimated.

Using this expression for $$\hat{\sigma}_b^2,$$

the error in the model for an arbitrary value of $t_2$ may be estimated as:

$$\hat{\sigma}_m^2(t_2) = \frac{\hat{\sigma}^2}{n_{eff}} + \hat{\sigma}_b^2 \cdot \left(t_{2,i} - \overline{t_2}\right)^2$$

Note that this expression has a minimum at $t_2 = \overline{t_2}$, where the model error reduces to $$\frac{\hat{\sigma}^2}{n_{eff}}:$$

the sample variance divided by the effective number of data points.

As moving further away from $\overline{t_2}$, the model error increases at a rate determined by the estimated error in the drift.

This equation may be used for the assessment of the synchronization result by setting a threshold on the maximum model error $$\max_{t_2} \hat{\sigma}_m^2(t_2),$$

which may occur either at the start or the end of the overlapping part of the recordings from the first and second sensors 11, 12, given by $t_{2,min} = \max(0, -\Delta T_S - \hat{A})$ and $t_{2,max} = \min(D_2, D_1 - \Delta T_S - \hat{A})$, respectively.

This quality measure may assume that the signal lengths are restricted to the actual physiological signal durations. In case the sensors records 16 hours of data regardless of whether or not the sensors are being worn, the signals may be trimmed using the available lead-off detections before using the synchronization method. This may be a safe choice since it reduces any risk of detecting false matches in noise.

Finally, the synchronization result may be marked as invalid if the estimated clock drift is outside of the specified range. If the initial time offset is outside of the specified range, the sequence pattern matching will already fail, and either no data points, or a small number of highly scattered data points, will be available for fitting a model. The implemented measures for quality assessment may in such case reject the result.

The goal of the synchronization is to be able to represent the signals recorded by the second sensor in the time domain of the first sensor. Starting out with a signal $S2(n)$ and the identified model parameters, it may be required to resample $S2(n)$ by a factor $(1+\hat{b})$, and shift the result in time by a time shift $\hat{a}$. In one implementation, the resampling may be implemented using cubic spline interpolation for all physiological/physical signals; and nearest neighbor interpolation for all categorical signals (e.g. the lead-off flag of a biopotential signal).

The synchronization may further rely on matching segments of uniformly sampled heart rate sequences r1 and r2. These sequences are derived from the output of a heartbeat detector.

The heartbeat detector detects individual heart beats in either an ECG signal or a PPG signal. The beats are output as a sequence of time stamped events, possibly extended with more detailed properties of each individual beat.

A transformation scheme may be tailored to achieve the highest accuracy in the present context of signal synchronization. It is based on the sample-and-hold method as illustrated in FIG. 7.

Figure 7:
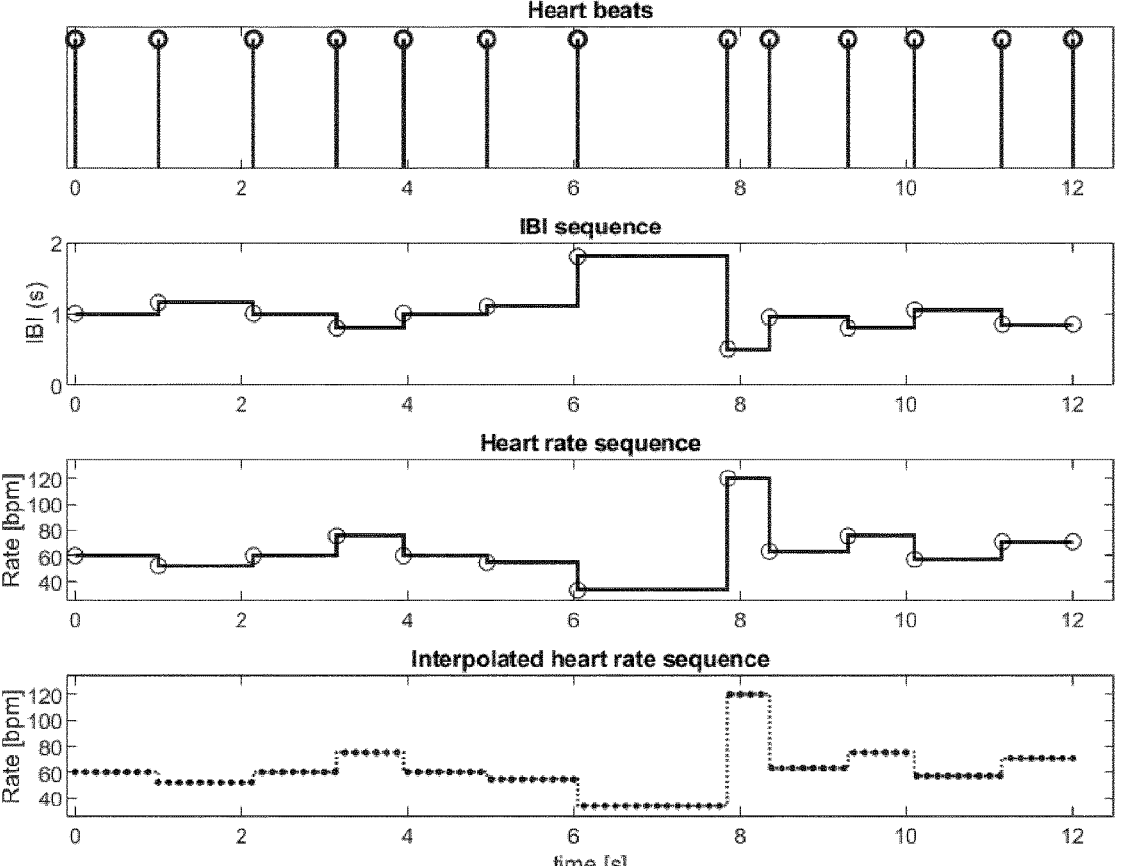
FIG. 7 shows plots of heart rate sequence according to one embodiment of the invention.

In FIG. 7, the top pane shows a short sequence of detected heartbeat events. The second pane shows the sequence of inter beat intervals (IBI), where each value represents the time difference between the current and the next beat.

The third pane shows the corresponding instantaneous heart rate sequence, derived from the IBI sequence. The bottom pane finally shows how the instantaneous heart rate sequence is interpolated to a uniform grid using sample-and-hold.

To achieve an accurate synchronization, a sample rate of 32 Hz may be used. In order to enable an efficient implementation and reduce the computational load of the high number of signal correlations (MADs) in the method, a two-step approach may be used. In a first step, the pattern matching uses only ⅛th of the samples, resulting in a sample rate of only 4 Hz. Having found the minimum, the search is refined locally using the original sample rate of 32 Hz.

Short gaps in the heartbeat input sequence (caused by e.g. missed beats or motion artefact) may be interpolated. Extended gaps may not be interpolated to prevent erroneous pattern matches on interpolated segments of the heart rate sequences. Instead, extended gaps may be marked by a dedicated heart rate value of zero, and excluded from matching.

As described above, the synchronization method may use several methods to assess the validity of its estimated parameters. There is however also a more direct way to evaluate the result, which is presented below. Such valida-tion may be used offline to validate the outcome.

Individual heart beats in the two synchronized sequences may be matched, after resampling of the second output signal. For this purpose the beat detector is applied to the first output signal S1 and to the resampled version of the second output signal S2.

Since the two sequences are already well synchronized, matching individual heart beats is easy. For every beat in second hear rate sequence signal r2 having a time stamp $t_2(k)$, the corresponding beat in the first heart rate sequence signal r1 is found by selecting the beat having the smallest absolute time difference, which is then assigned to $\Delta t(k)$.

The result may be visualized in two ways: as a time graph showing $\Delta t(k)$ as a function of $t_2(k)$, and in the form of a histogram. Moreover, the sample time bias and standard deviation may be calculated as quantitative measures.

Figure 8:
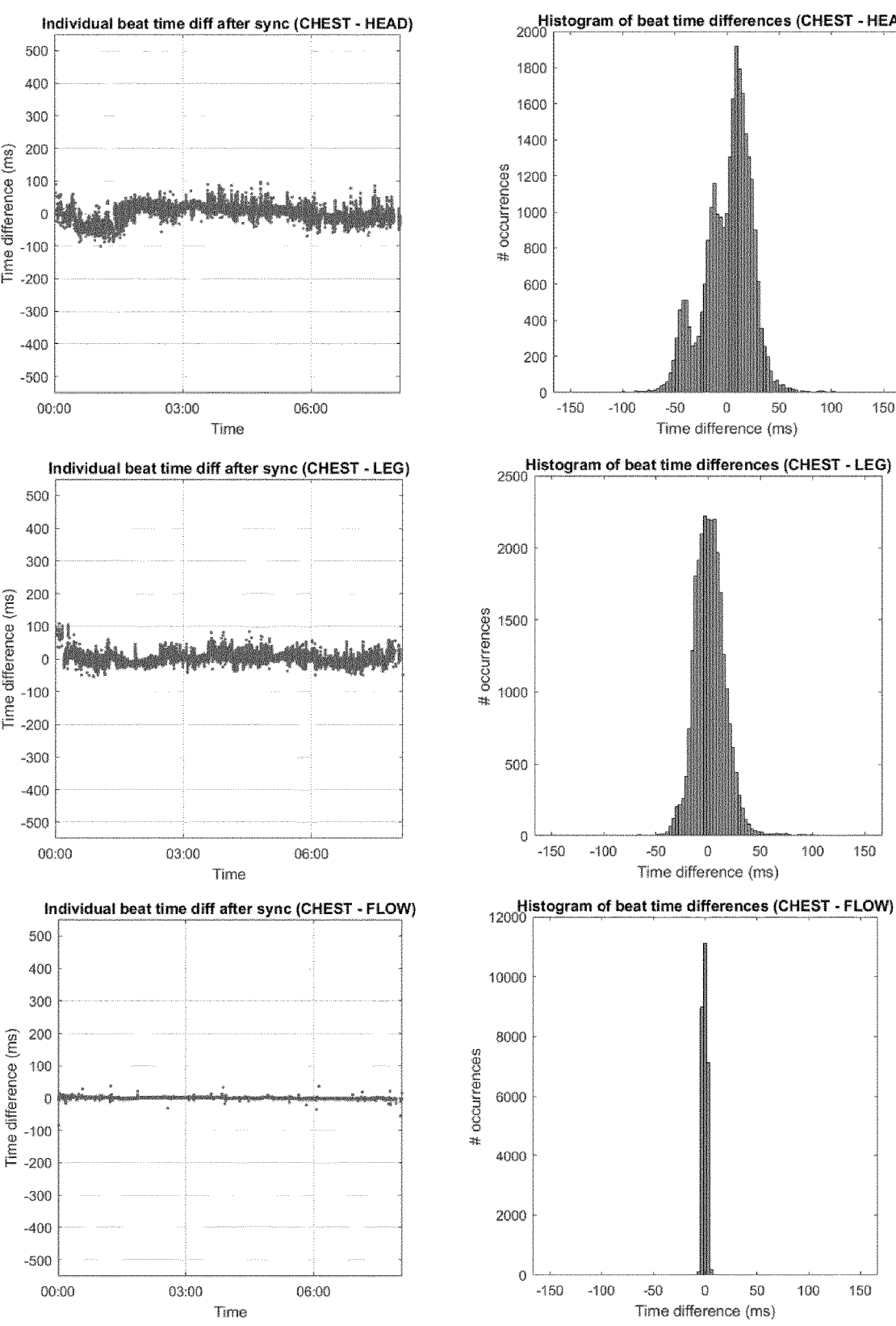
FIG. 8 shows a visualization of synchronization result according to one embodiment of the invention.

For an explementary embodiment, such visualization is illustrated in FIG. 8. A chest sensor was used as reference, i.e. as first sensor. The top pane shows results for a head sensor; results for a leg sensor are shown in the middle pane, and the bottom pane shows the results for a flow sensor.

In the drawings and specification, there have been dis-closed preferred embodiments and examples of the inven-tion and, although specific terms are employed, they are used in a generic and descriptive sense only and not for the purpose of limitation, the scope of the invention being set forth in the following claims.

The invention claimed is:

1. A method of synchronizing output signals from a plurality of sensors each measuring a heart rate derivable physiological signal of a subject along with a physiological signal of interest, comprising the steps of:
   acquiring a first output signal using a first sensor config-ured to measure a heartbeat derivable physiological signal of a subject along with a first physiological signal of interest;
   acquiring a second output signal using a second sensor configured to measure a heartbeat derivable physiologi-cal signal of the subject along with a second physi-ological signal of interest,
   wherein each of the first and second sensor comprises an independent clock for associating the signals measured by the first and second sensors with a respective time domain, the method further comprising the steps of:
   determining a first heart rate sequence signal from the first output signal;
   determining a second heart rate sequence signal from the second output signal;
   identifying timings of at least one heart rate event in the respective first and second heart rate sequence signals; and determining a first time domain transformation for the time domain of the second output signal to the time domain of the first output signal using a model fitted to the timings of the at least one heart rate event in the respective first and second heart rate sequence signals,
   capturing a first physiological signal of interest, using the first sensor that is different from the first output signal;
   capturing a second physiological signal of interest using the second sensor that is different from the second output signal; and
   synchronizing the second physiological signal of interest to the first physiological signal of interest by applying model parameters of the model to the second physi-ological signal of interest.

2. The method according to claim 1, wherein the step of determining a first time domain transformation comprises the steps of identifying a first time difference between the timing of a first heart rate event in the first heart rate sequence signal and the timing of a corresponding first heart rate event in the second heart rate sequence signal, and forming the model based on the first time difference.

3. The method according to claim 2, wherein the step of determining a first time domain transformation further com-prises identifying a second time difference between the timing of a second heart rate event in the first heart rate sequence signal and the timing of a corresponding second heart rate event in the second heart rate sequence signal, and the step of forming the model comprises a step of forming a linear model based on the first and second time differences.

4. The method to claim 3, wherein the linear model is described as A+Bt2, wherein A represents an initial time offset between the first and second heart rate sequence signals, B represents a clock drift of the clock of the second sensor based on the first and second time differences, and t2 is the time instant of the time domain of the second output signal.

5. The method according to claim 1, wherein the first heart rate sequence signal is based on a portion of the first output signal and the second heart rate sequence signal is based on a portion of the second output signal.

6. The method according to claim 1, wherein the method further comprises a step of resampling the second output signal based on the first time domain transformation.

7. The method according to claim 1, wherein at least one of the first and second sensors providing the first and second output signals is a body-worn sensor.

8. The method according to claim 7, wherein the body-worn sensor is configured to be worn on the chest, the head, and/or a leg of a subject.

9. The method according to claim 1, wherein at least one of the sensors provides an output signal is an ECG-measur-ing sensor.

10. The method according to claim 1, wherein at least one of the sensors provides an output signal is a PPG-measuring sensor.

11. The method according to claim 1, further comprising the steps of;
   providing a third and fourth output signal each acquired using a respective third and fourth sensor measuring a heart rate derivable physiological signal of a subject; and
   determining a second and a third time domain transfor-mation for the time domains of the third and fourth output signals to the time domain of the first output signal using respective models fitted to the timings of heartbeats in the respective first and third heart rate sequence signals and first and fourth heart rate sequence signals, respectively.

12. The method according to claim 11, wherein two of the first, second, third, and fourth sensors are ECG-measuring sensors.

13. The method according to claim 11, wherein two of the first, second, third, and fourth sensors are PPG-measuring sensors.

14. The method according to claim 1, wherein the method is applied to a measurement of a subject during a sleep cycle.

15. A system for synchronizing sensor output signals comprising:

at least a first and a second sensor, each configured to measure a heartbeat derivable physiological signal of a subject along with a physiological signal of interest and to acquire a first and a second output signal, respectively, wherein each sensor comprises an independent clock for associating the signals measured by the first and second sensors with a respective time domain; and a processing unit configured to:

receive the first and second output signals;

determine a first heart rate sequence signal from the first output signal;

determine a second heart rate sequence signal from the second output signal;

identify timings of at least one heart rate event in the respective first and second heart rate sequence signals; and determine a first time domain transformation for the time domain of the second output signal to the time domain of the first output signal using a model fitted to the timings of the at least one heart rate event in the respective first and second heart rate sequence signals;

wherein the first sensor is configured to capture a first physiological signal of interest that is different from the first output signal, the second sensor is configured to capture a second physiological signal of interest that is different from the first output signal, and the processing unit is configured to synchronize the second physiological signal of interest to the first physiological signal of interest by applying model parameters of the model to the second physiological signal of interest.

* * * * *